United States Patent
Hofer et al.

(10) Patent No.: US 7,217,681 B2
(45) Date of Patent: May 15, 2007

(54) PESTICIDAL COMPOSITION AND METHOD FOR FUNGAL CONTROL

(75) Inventors: Dieter Hofer, Basel (CH); David Long, Greensboro, NC (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 13 days.

(21) Appl. No.: 11/028,769

(22) Filed: Jan. 4, 2005

(65) Prior Publication Data

US 2005/0209304 A1    Sep. 22, 2005

Related U.S. Application Data

(60) Provisional application No. 60/553,462, filed on Mar. 16, 2004.

(30) Foreign Application Priority Data

Jun. 7, 2004   (EP)   .................. PCT/EP04/00611

(51) Int. Cl.
*A61K 31/33*   (2006.01)
*A01N 25/26*   (2006.01)
*A01N 43/00*   (2006.01)

(52) U.S. Cl. .............. 504/100; 504/129; 514/183
(58) Field of Classification Search .............. 424/405; 514/183; 504/100, 129
See application file for complete search history.

(56) References Cited

U.S. PATENT DOCUMENTS

2005/0096224 A1*   5/2005   Dawkins .................. 504/100

FOREIGN PATENT DOCUMENTS

WO   9933343   7/1999

* cited by examiner

*Primary Examiner*—Alton Pryor
(74) *Attorney, Agent, or Firm*—Jacqueline Haley

(57) ABSTRACT

A method of reducing nematode-fungal interaction in a plant by treating a propagation material thereof with a nematicidally effective amount of a nematicide, and a fungicidally effective amount of a fungicide before the material is planted or sown.

14 Claims, No Drawings

PESTICIDAL COMPOSITION AND METHOD FOR FUNGAL CONTROL

This application claims priority to U.S. provisional application Ser. No. 60/553,462 filed on Mar. 16, 2004 and to international application Ser. No. PCT/EP2004/00611 filed on Jun. 7, 2004.

FIELD OF THE INVENTION

The present invention relates to pesticidal composition that is suitable for controlling nematodes and microorganisms (especially phytopathogenic fungi) comprising (a) at least one nematicide and (b) at least one fungicide. The pesticidal composition is particularly suitable for the protection of plant propagation materials such as seed.

In particular, the present invention relates to a method of reducing nematode fungal interaction in a plant by treating a propagation material thereof with a nematicidally effective amount of a nematicide, and a fungicidally effective amount of a fungicide before the material is planted or sown.

BACKGROUND OF THE INVENTION

Certain mixtures of active ingredients for controlling pests are described in the literature. The biological properties of those known mixtures are not entirely satisfactory in the areas of nematode control, phytotoxicity, loading rates and environmental and worker exposure, for example. The protection of plant propagation materials (seed treatments) with pesticides are target applications which partially address the need for a reduction of environmental and worker exposure when used alone or in conjunction with foliar or in-furrow pesticide applications. However, there is also a need to make available other mixtures which reduce the need for older acutely toxic pesticides and to reduce loading rates. Among the older nematicides, the following may be mentioned: methyl bromide, metham sodium, ethoprop, carbofuran, aldicarb, fenamiphos and oxamyl. Further, interactions between nematode and fungal pathogens are recognized as causing damage in excess of the additive amount expected of the individual nematodes and fungal pathogens (Compendium of Cotton Disease, 2nd edn., edited by T L Kirkpatrick & C S Rothrock, The American Phytopathological Society, pp. 46–48). Accordingly, there is a need to provide pesticide compositions and methods for the protection of plant propagation materials, especially those compositions having improved biological properties, for example synergistic pesticidal properties, especially for controlling nematodes and fungal pathogens. That problem is solved according to the invention by the provision of the present pesticidal composition.

SUMMARY OF THE INVENTION

The present invention provides a composition for controlling nematodes and microorganisms, which composition comprises: (A) at least one nematicidally active macrolide compound, and (B) at least one fungicidally active compound selected from the phenylamides, the phenylpyrroles and the strobilurins.

More specifically, the present invention provides a composition for controlling nematodes and microorganisms, especially phytopathogenic fungi, that is particularly suitable for the protection of plant propagation materials such as crop seeds. The pesticidal composition of the present invention comprises: (A) an nematicidally effective amount of at least one macrolide compound, and (B) a fungicidally effective amount of at least one fungicide compound selected from: (B1) at least one phenylamide (acylalanine type), (B2) at least one phenylpyrrole and (B3) at least one strobilurin. In an embodiment, at least three fungicide compounds are selected from (B1), (B2) and (B3), wherein at least one is selected from each of (B1), (B2) and (B3), and thereby provide an at least quaternary pesticidal composition.

The invention also relates to a process for protecting the plant propagation materials and the plants resulting therefrom against nematodes and fungal diseases using a pesticidal composition according to the invention. It also relates to the said plant propagation materials coated with the said pesticidal composition.

The present invention makes it possible to dress or treat seeds and other plant propagation materials with lower amounts of older acutely toxic biocides than is known from the prior art and, in most cases, replaces such older acutely toxic biocides; the invention therefore represents a material enrichment of the art.

The present invention further provides a method of reducing nematode fungal interactions in a plant by treating a propagation material thereof with a nematicidally effective amount of a nematicide, and a fungicidally effective amount of a fungicide before the material is planted or sown.

DESCRIPTION OF SPECIFIC EMBODIMENTS

Nematicide Compound (A)

The pesticidal compositions according to the invention comprise as nematicidally active ingredient (A) a compound having nematicide activity as a plant propagation material treatment, preferably at least one macrolide compound selected from abamectin, emamectin benzoate and spinosad.

Abamectin is a preferred macrolide compound (A).

The present invention also provides protection of plants against attack by nematodes by the treatment of plant propagation material thereof with a composition according to the present invention.

Fungicide Components (B)

The pesticidal compositions according to the invention comprise as fungicidally active ingredient (B): at least one fungicidal compound selected from (B1), (B2) and (B3), wherein:

(B1) is at least one phenylamide (acylalanine type) of the formula (III):

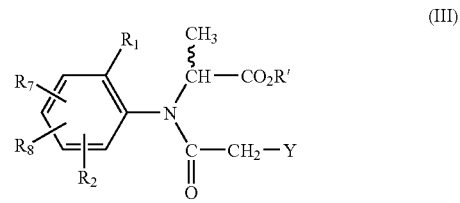

wherein $R_1$ is methyl; $R_2$ is in ortho position to the amino group and is methyl, ethyl or chlorine; $R_7$ and $R_8$ independently are hydrogen or methyl; R' is methyl; and Y is —$OR_4$ or —$SR_4$ in which $R_4$ is methyl, ethyl, propyl, isoprop yl, butyl, sec. butyl or tert. butyl; and enantiomers thereof; in free from or in salt form.

Preferred phenylamide derivatives of formula (III) usable in the compositions and methods falling within the scope of the present invention include metalaxyl (516); metalaxyl consisting of more than 70% by weight of the R-enantiomer; metalaxyl consisting of more than 85% by weight of the R-enantiomer; metalaxyl consisting of more than 92% by weight of the R-enantiomer; metalaxyl consisting of more than 97% by weight of the R-enantiomer; and mefenoxam (i.e., R-metalaxyl or metalaxyl-M (517)).

(B2) is at least one phenylpyrrole of the formula (IV):

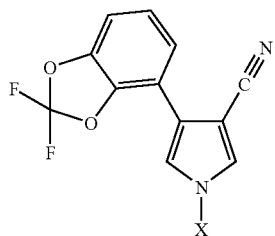

wherein X is hydrogen or CO—R$_1$, wherein R$_1$ is C$_1$–C$_6$alkyl which is unsubstituted or substituted by halogen or C$_1$–C$_3$alkoxy; or is C$_3$–C$_6$alkenyl, C$_3$–C$_6$alkynyl, or C$_1$–C$_6$alkoxy which is unsubstituted or substituted by halogen or C$_1$–C$_3$alkoxy; or is C$_3$–C$_6$alkenyloxy, or C$_3$–C$_6$cycloalkyl; in free from or in salt form.

A specific phenylpyrrole (IV) usable in the compositions and methods falling within the scope of the present invention is fludioxonil (368).

(B3) is at least one strobilurin compound selected from azoxystrobin (47), dimoxystrobin, fluoxastrobin, kresoxim-methyl, metominostrobin, orysastrobin, picoxystrobin, pyraclostrobin and trifloxystrobin.

The compounds of the formula (III) are known, for instance, from U.S. Pat. No. 4,151,299;

The compounds of the formula (IV) are known, for example, from U.S. Pat. No. 4,705,800;

Fludioxonil is known, for example, from The Pesticide Manual, 11th Ed. (1997), The British Crop Protection Council, London, page 566;

Metalaxyl is known, for example, from The Pesticide Manual, 11th Ed. (1997), The British Crop Protection Council, London, page 792;

R-metalaxyl (mefenoxam) is known, for example, from The Pesticide Manual, 11th Ed. (1997), The British Crop Protection Council, London, page 794;

Azoxystrobin is known, for example, from The Pesticide Manual, 11th Ed. (1997), The British Crop Protection Council, London, page 70;

Dimoxystrobin is known, for example, from the e-Pesticide Manual, version 3.0, 13th Edition, Ed. CDC Tomlin, British Crop Protection Council, 2003–04, entry 266;

Fluoxastrobin is known, for example, from the e-Pesticide Manual, version 3.0, 13th Edition, Ed. CDC Tomlin, British Crop Protection Council, 2003–04, entry 382;

Kresoxim-methyl is known, for example, from the e-Pesticide Manual, version 3.0, 13th Edition, Ed. CDC Tomlin, British Crop Protection Council, 2003–04, entry 485;

Metominostrobin is known, for example, from the e-Pesticide Manual, version 3.0, 13th Edition, Ed. CDC Tomlin, British Crop Protection Council, 2003–04, entry 551;

Picoxystrobin is known, for example, from the e-Pesticide Manual, version 3.0, 13th Edition, Ed. CDC Tomlin, British Crop Protection Council, 2003–04, entry 647;

Pyraclostrobin is known, for example, from the e-Pesticide Manual, version 3.0, 13th Edition, Ed. CDC Tomlin, British Crop Protection Council, 2003–04, entry 690; and Trifloxystrobin is known, for example, from the e-Pesticide Manual, version 3.0, 13th Edition, Ed. CDC Tomlin, British Crop Protection Council, 2003–04, entry 832.

A description of pesticides (e.g., fungicides, insecticides, nematicides) can be found in the e-Pesticide Manual, version 3.1, 13th Edition, Ed. CDC Tomlin, British Crop Protection Council, 2004–05. The number following the compound name, if indicated, is the entry number given in the Pesticide Manual.

A.I. Combination

Surprisingly, it has been found that the combination of at least one nematicide active ingredient (A) with at least one fungicide active ingredient selected from (B1), (B2) and (B3) results in a quite unexpectedly enhanced action against nematodes and microorganisms such as seed-borne and soil-borne fungi and/or provides other unexpected advantages when used in connection with plant propagation materials. The increase in action and/or other advantageous properties achieved with the combination according to the invention is significantly greater than the activity to be expected by the individual components, i.e. the activity is enhanced synergistically which, inter alia, extends the boundaries of the pesticidal activity of the compounds.

The inventive mixture is particularly suitable for dressing applications on plant propagation material. The latter term embraces seeds of all kinds (fruit, tubers, grains), cuttings, cut shoots and the like. Seeds are preferred. One particular field of application is the treatment of all kinds of seeds, in particular the seed treatment of cotton, fruiting vegetables incl. tomatoes and peppers, cucurbit vegetables incl. melons, cantaloupes, squash and cucumber.

In addition to the at least two component mixture, this invention also relates to a method of controlling fungi and nematodes, which comprises treating a site, for example a plant or a plant propagation material (especially seed), that is infested or liable to be infested by fungi and nematodes with: (1) at least one nematicidal active ingredient (A) and (2) at least one fungicidal active ingredient (B) in any desired sequence or simultaneously.

When three fungicides are employed together, advantageous mixing ratios by weight of the three fungicide active ingredients are (B1):(B2):(B3)=from 10:1:1 to 1:1:10 and to 1:10:1. For example, ratios of 1 g: 2.5 g: 1 g a.i./100 kg seed or 1 g: 2.5 g: 2.5 g a.i./100 kg seed or 1 g: 2.5 g: 5 g a.i./100 kg seed or 1 g: 2.5 g: 10 g a.i./100 kg of seed are suitable.

The nematicide active ingredient generally is applied in a mixing ratio by weight (A):(B) (where (B) includes all of (B1), (B2) and/or (B3) that is employed) of from 200:1 to 2.5:1. For example, in one embodiment, abamectin (A) is applied at a rate of from 100 g–400 g a.i./100 Kg seed. As a specific example, abamectin is applied at a rate of 100 g/100 Kg seed; R-metalaxyl (B1) is applied at a rate of from 7–10 g a.i./100 Kg seed; fludioxonil (B2) is applied at a rate of from 2–5 g a.i./100 Kg seed, and azoxystrobin (B3) is applied at a rate of from 15–20 g a.i./100 Kg seed. The mixing ratio of the ingredients of (A):(B1):(B2):(B3) is (100–400 g):(7–10 g):(2–5 g):(15–20 g) per 100 Kg of seed and preferably (A):(B1):(B2):(B3) is (100 g):(7.5 g):(2.5 g):(15 g) per 100 Kg of seed. In one embodiment, abamectin is applied at 0.1 to 0.15 mg/seed or, in particular, 0.1 mg/seed.

In particular, it has now been found, surprisingly, that, for example, the pesticidal activity of the compositions according to the invention, compared with the pesticidal activity of the individual components, is not merely additive, as may essentially be expected, but that a synergistic effect exists.

The term "synergistic" is not, however, in any way limited in this context to the pesticidal activity, but refers equally to other advantageous properties of the compositions according to the invention as compared with the individual components. Examples of such advantageous properties that may be mentioned are: a broadening of the spectrum of pesticidal activity to other pests, for example to resistant strains; a reduction in the rate of application of the active ingredients; adequate control of the pests with the aid of the compositions according to the invention, even at a rate of application at which the individual compounds are totally ineffective; advantageous behavior during formulating and/or upon application, for example upon grinding, sieving, emulsifying, dissolving or dispersing; increased storage stability; improved stability to light; more advantageous degradability; improved toxicological and/or ecotoxicological behavior; improved crop characteristics including: emergence, crop yields, plant stand, more developed root system, tillering increase, increase in plant height, bigger leaf blade, less dead basal leaves, stronger tillers, greener leaf color, less fertilizers needed, less seeds needed, more productive tillers, earlier flowering, early grain maturity, less plant verse (lodging), increased shoot growth, improved plant vigor, and early germination; or any other advantages familiar to a person skilled in the art.

The active ingredient combination utilized in the seed treatment composition according to the invention preferably comprises abamectin, R-metalaxyl, fludioxonil and azoxystrobin.

In one embodiment, at least one other antimicrobially active substance (C) is employed with to the at least two-component mixture of (A) and (B) to increase the spectrum of action or to achieve particular effects such as, for example, allowing the application rate of the fungicides to be reduced while still maintaining an equally good fungicidal activity. Suitable additional fungicides classes include the triazoles such as, for example, myclobutanil which can be employed at a rate of from 21–30 g a.i./100 Kg seed. Other fungicides that may be mentioned include triadimenol, TCMTB, PCNB, carboxin and chloroneb.

In another embodiment, at least one insecticidally active substance (D) is employed with the at least two-component mixture of (A) and (B). Suitable insecticide classes include the neonicotinoids, such as imidacloprid, clothianidin and thiamethoxam; pyrethrins and synthetic pyrethroids, such as tefluthrin (769) and lamda cyhalothrin (198); and fipronil (354). For example, thiamethoxam is employed at a rate of from 300–500 g a.i./100 Kg seed.

In one embodiment, the seed treatment composition and method(s) of the invention are combined with one or more foliar and/or in-furrow insecticide and/or fungicide treatments. Suitable insecticides include, for example, Temik® (aldicarb), thiamethoxam, imidacloprid and clothianidin. Suitable fungicides include metalaxyl, R-metalaxyl, the stobilurins such as azoxystrobin, the triazoles such as myclobutanil, fludioxonil, triadimenol, TCMTB, PCNB, carboxin and chloroneb.

Fungal Pests

The compositions according to the invention are especially active against fungi, in particular of the oomycetes which belong to the class of phycomycetes (e.g., *Phytophthora* spp., *Peronospora* spp., *Pseudoperonospora* spp., *Pythium* spp. [i.e. *P. utimum, P. aphanidermatum, P. graminicola, P. irregulare*) or *Plasmopara* sp.), basidiomycete (i.e. *Puccinia* spp. [ *P. recondita, P. striformis*, and *P. graminis*], *Tilletia* spp. [i.e *T. caries* and *T. contreversa*], *Ustilago* spp. [i.e. *U. maydis, U. nuda, U. hordei*, and *U. avenae*]), ascomycete (such as *Gibberella* spp. [i.e. *G. fujikuroi, G. roseum*] *Glomerella* spp. [i.e. *G. gossypii*]) , adelomycete or Fungi Imperfecti type, such as *Rhizoctonia* spp. (i.e. *R. solani, R. cerealis* and *R. zea*), *Fusarium* spp. (i.e. *F. solani, F. oxysporum, F. roseum, F. nivale, F. moniliforme, F. proliferatum, F. graminearum, F. subglutinans*), *Helminthosporium* spp. (i.e. *H. oryzae, H. teres, H. gramineum* and *H. sativum*), *Phoma* spp. (i.e. *P. betae, P. foveata* and *P. lingam*), *Alternaria* spp. (i.e. *A. solani, A. macrospora* and *A. alternata*), *Colletotriuchum* (i.e. *C. graminicola, C. coccodes, C. capsici, C. gossypii* and *C. truncatum*), *Erysiphe* spp. (i.e. *E. graminis* and *E. cichoracearum*) *Gaeumannomyces* spp. (i.e. *G. graminis* var *graminis* and *G. graminis* var. *tritici*), *Botrytis* spp. (i.e. *B. cinerea*), *Pyricularia* spp. (i.e. *P. grisea* and *P. oryzae*), *Cercosoora* spp. (i.e. *C. beticola*), *Rhinchosporium* spp. (i.e. *R. secalis*), *Pyrenophora* spp. (i.e. *P. avenae*), *Septoria* spp. (i.e. *S. tritici* and *S. avenae*), *Whetzelinia* spp. (i.e. *W. sclerotiorum*), *Microdochium* spp., *Mycosohaerella* spp., (i.e. *M. fijiensis*), *Aspergillus* spp. (i.e. *A. niger* and *A. flavus*), *Cercospora* spp. (i.e. *C. arachidicola* and *C. gossypina*), *Claviceps* spp., *Cladosporium* spp. (i.e. *C. herbarum*), *Penicillium* spp., *Pestalozzia* sp, *Verticillium* spp. (i.e. *V. dahliae*), *Ascochyta* spp. (i.e. *A. pisi* and *A. gossypii*), *Guignardia* spp. (i.e. *G. bidwellii*), *Corticium rolfsii, Phomposis* spp. (i.e. *P. viticola*), *Sclerotinia* spp. (i.e. *S. sclerotiorum* and *S. minor*), *Sclerotinia minor, Coryneum cardinale, Acrostalagmus koningi, Corticium roffsii, Diplodia* spp. (i.e. *D. natalensis*), *Hormodendron cladosporioides, Myrothecium* spp. (i.e. *M. verrucaria*), *Paecylomyces varioti, Pellicularia sasakii, Phellinus megaloporus, Septoria* spp., *Sclerotium* spp. (i.e. *S. rolfsii*), *Stachybotris atra, Trichoderma* ssp. (i.e. *T. pseudokoningi*), *Thielaviopsis basicola* and *Trichothecium roseum*.

The compositions according to the invention are particularly suited for the reductive, preventive and the curative protection of the plant propagation material against fungi and fungal diseases including: damping off (e.g., *Fusarium* sp., *Pythium* sp., *Rhizoctonia* sp.), root rot (e.g., *Pythium* sp., *Fusarium* sp., *Gibberella* sp.), and seed or soil borne blackleg (*Leptosphaeria maculans*) diseases of vegetable organisms and plants in general, and especially of crops such as cotton and also soya and maize.

Nematode Pests

Examples of representatives of the class Nematoda which may be controlled by the compositions of the invention include, for example: root knot nematodes, stem eelworms and foliar nematodes; especially *Heterodera* spp., for example *Heterodera schachtii, Heterodora avenae* and *Heterodora trifolii; Hoplolaimus* spp. such as *Hoplolaimus galeatus* and *Hoplolaimus columbus; Globodera* spp., for example *Globodera rostochiensis; Meloidogyne* spp., for example *Meloidogyne incoginita* and *Meloidogyne javanica; Radopholus* spp., for example *Radopholus similis; Rotylenchulus* spp. such as *R. reniformis; Pratylenchus* spp., for example *Pratylenchus neglectans* and *Pratylenchus penetrans; Tylenchulus* spp., for example *Tylenchulus semipenetrans; Belonolaimus* spp.; *Longidorus* spp.; *Trichodorus* spp.; *Xiphinema* spp.; *Ditylenchus* spp.; *Aphelenchoides* spp.; and *Anguina* spp.; in particular *Meloidogyne* spp., for example *Meloidogyne incognita*, and *Heterodera* spp., for example *Heterodera glycines*.

Target Crops

Target crops within the scope of this invention are, for example, the following plant species: beet (sugar beet and fodder beet), oil plants (canola, rape, mustard seed, poppy, olives, sunflowers, coconut, castor oil plants, cocoa beans, groundnuts and soya). There also may be mentioned peanuts, wheat sorghum, cotton, corn, soybeans, tobacco, cole, cabbages, onions and carrots.

Other suitable crops within the scope of the invention include potato, mint, grass forage and hay as well as the herb subgroup.

In addition, the crops listed in the crop group tables in 40 CFR Sec. 180.41 (1995) are noted. 40 CFR Sec. 180.41 (1995) and the Federal Register: May 17, 1995 (vol. 60, no. 95) pp. 26625–26643 are fully incorporated by reference herein for their disclosure relating to useful crop plants:

(1) Crop Group 5: *Brassica* (Cole) Leafy Vegetables Group, for example, broccoli, cauliflower; cabbage; and mustard greens;
(2) Crop Group 9: Cucurbit Vegetables Group, for example, cucumber, melons, cantaloupe, muskmelon, squash incl. summer squash;
(3) Crop Group 11: Pome Fruits Group, for example, apple and pear;
(4) Crop Group 15: Cereal Grains Group, for example, corn and rice.

There also may be mentioned the fruiting vegetables group, for example, tomatoes and peppers.

The following plants are to be regarded as being particularly suitable target crops for the at least quaternary pesticide compositions of the invention: plant propagation materials (such as seeds) of oil plants (canola, rape, mustard seed, poppy, olives, sunflowers, coconut, castor oil plants, cocoa beans, groundnuts).

The target crops and the seeds treated in accordance with the invention include conventional as well as genetically enhanced or engineered varieties such as, for example, insect resistant (e.g., Bt. And VIP varieties) as well as disease resistant, herbicide tolerant and nematode tolerant varieties. By way of example, suitable genetically enhanced or engineered crops varieties include the Stoneville 5599BR cotton and Stoneville 4892BR cotton varieties.

Cotton is especially prone to nematode-fungal interaction damage, and the present invention of treatment of the plant propagation material with a nematicide shows a reduction of the interaction.

Seed Treatment

The pesticidal composition according to the invention has proved especially advantageous for protecting seeds, in particular, seeds of cotton, fruiting vegetables incl. tomatoes and peppers, cucurbit vegetables incl. melons, cantaloupes, squash and cucumber. However, the inventive composition is also suitable for direct treatment of the soil or of other parts of the plant. The inventive composition is well tolerated by plants, and is ecologically acceptable.

The subject of the invention is also a method for protecting the multiplication products of plants (plant propagation materials) and the plants resulting therefrom against nematodes and fungal diseases, wherein the said multiplication products are coated with a nematicidal and fungicidal and substantially non-phytotoxic composition according to the invention.

The at least binary pesticidal composition according to the invention is usually employed together with the adjuvants customary in formulation technology. The combination of the active ingredients (A) and at least one of (B1), (B2) and (B3) are normally applied to plant propagation material in the form of compositions, but also can be applied to the seed or to the locus of propagation thereof (such as a furrow), simultaneously or in succession, with further compounds. These further compounds can be fertilizers or micronutrient donors or other preparations that influence plant growth. They can also be selective herbicides, insecticides, fungicides, bactericides, insect growth regulators, plant growth regulators, foliar or soil applied nematicides, molluscicides or mixtures of several of these preparations, if desired, together with further carriers, surfactants or application-promoting adjuvants customarily employed in the art of formulation. In addition, there may be mentioned inoculants, brighteners and polymers.

This invention also includes suitable agricultural compositions for controlling nematodes and fungi on or in seed consisting essentially of an at least binary pesticidal composition of this invention plus a suitable inert surfactant or an suitable inert liquid or a solid carrier. As used herein, the phrase "consisting essentially of" does not exclude the presence of other active pesticidal materials or conventional formulating ingredients.

The active components (A) and at least one of (B1), (B2) and (B3) are processed in known manner to give, for example, emulsifiable concentrates, suspoemulsions, spreadable pastes, directly sprayable or dilutable solutions, dilute emulsions, wettable powders, soluble powders, dusts, granules, and also for encapsulation in, for example, polymeric substances or in the form of so-called tank mixes which are prepared by concomitant dilution of the separately formulated components with water immediately prior to application. The application methods, such as spraying, misting, atomising, broadcasting, brushing or pouring, and the nature of the composition are adapted to suit the intended aims and the prevailing circumstances. Optimum rates of application of the inventive composition, for a particular target nematode and set of disease conditions, can be determined easily and without undue experimentation by simple ranging studies carried out in greenhouse or field settings. In general, favorable rates of application are 0.0005 to not more than 0.5 kg, in particular 0.001–0.02 kg of each active ingredient (B1), (B2) and (B3) per 100 kg of propagation material to be protected. With respect to the active ingredient (A), the favorable rates of application can range from 0.005 to not more than 0.8 kg, in particular 0.01–0.5 kg, more particularly 0.1–0.4 kg per 100 kg of propagation material to be protected. However, the application conditions depend essentially on the nature (surface area, consistency, moisture content) of the material and on its environmental factors. Accordingly, within these ranges, those skilled in the art will choose, on the basis of their general body of knowledge and, where appropriate, a few experiments, doses which are non-phytotoxic but effective from a fungicidal and/or nematicidal standpoint.

The term "plant propagation material" is understood to denote all the generative parts of the plant such as seeds which can be used for the multiplication of the latter and vegetative plant material such as cuttings and tubers (for example potatoes). There may be mentioned, e.g., the seeds (in the strict sense), roots, fruits, tubers, bulbs, rhizomes, parts of plants. Germinated plants and young plants which are to be transplanted after germination or after emergence from the soil, may also be mentioned. These young plants may be protected before transplantation by a total or partial treatment by immersion.

The techniques of seed treatment application are well known to those skilled in the art, and they may be used readily in the context of the present invention. The active ingredients can be formulated and applied as a slurry, a solid seed coating, a soak, or as a dust on the surface of the seed. There also may be mentioned, e.g., film-coating or encapsulation. The coating processes are well known in the art, and employ, for seeds, the techniques of film-coating or encapsulation, or for the other multiplication products, the techniques of immersion. Needless to say, the method of application of the compounds to the seed may be varied and the invention is intended to include any technique which is to be used.

A preferred method of applying the mixture according to the invention consists in spraying or wetting the plant propagation material with a liquid preparation, or mixing the plant material with a solid preparation of the active ingredients.

The compounds of this invention may be formulated or mixed in the seed treater tank or combined on the seed by overcoating with other seed treating agents. The agents to be mixed with the compounds of this invention may be for the control of pests, modification of growth, nutrition, or for the control of plant diseases.

Formulations

The formulations, i.e. the compositions, preparations or combinations containing the active ingredients (A), (B1), (B2) and (B3), as well as, if appropriate, suitable inert solid or liquid carriers, are prepared in a known manner, for example by intimately mixing and/or grinding the active ingredients with inert, agriculturally-acceptable extenders, for example with solid or liquid carriers and, if appropriate, surface-active compounds (surfactants). Such compositions may be advantageously formulated as flowable compositions, suspensions, microsuspensions, suspoemulsions; wettable powders, granulated concentrates, microemulsions and the like, all of which lend themselves to seed treatment application and provide the requisite plant protection.

The term "carrier" in the present description denotes a natural or synthetic, organic or inorganic material with which the active substance is combined in order to facilitate its application to the plant, to the seeds or to the soil. This carrier is hence generally inert, and it must be agriculturally acceptable, in particular to the plant being treated. The carrier may be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like).

Suitable liquid carriers are: aromatic hydrocarbons, in particular the fractions $C_8$ to $C_{12}$, such as xylene mixtures or substituted naphthalenes, phthalic esters such as dibutyl or dioctyl phthalate, aliphatic hydrocarbons such as cyclohexane or paraffins, alcohols and glycols as well as their ethers and esters, such as ethylene glycol monomethyl ether, ketones such as cyclohexanone, strongly polar solvents such as N-methyl-2-pyrrolidone, dimethyl sulfoxide or dimethylformamide, and, if appropriate, epoxidized vegetable oils or soybean oil; or water.

Solid carriers which may be used, for example for dusts and dispersible powders, are calcite, talc, kaolin, montmorillonite or attapulgite, highly-disperse silica or absorptive polymers. Possible particulate, adsorptive carriers for granules are pumice, crushed brick, sepiolite or bentonite, montmorillonite-type clay, and possible nonsorbent carrier materials are calcite or dolomite.

Suitable surface-active compounds are non-ionic, cationic and/or anionic surfactants having good emulsifying, dispersing and wetting properties, depending on the nature of the active ingredients (A), (B1), (B2) and (B3) to be formulated (whether individually or in one of the various permutations and combinations). Surfactants will also be understood as meaning mixtures of surfactants.

The surfactants customarily employed in formulation technology are described, inter alia, in the following publications:

"McCutcheon's Detergents and Emulsifiers Annual", MC Publishing Corp., Glen Rock, N.J., 1988. M. and J. Ash, "Encyclopedia of Surfactants", Vol. I–III, Chemical Publishing Co., New York, 1980–1981.

Among the suitable surfactants there may be mentioned, e.g., polyacrylic acid salts, lignosulphonic acid salts, phenolsulphonic or (mono- or di-alkyl)naphthalenesulphonic acid salts, laurylsulfate salts, polycondensates of ethylene oxide with lignosulphonic acid salts, polycondensates of ethylene oxide with fatty alcohols or with fatty acids or with fatty amines, substituted phenols (in particular alkylphenols or arylphenols such as mono- and di-(polyoxyalkylene alkylphenol)phosphates, polyoxyalkylene alkylphenol carboxylates or polyoxyalkylene alkylphenol sulfates), salts of sulphosuccinic acid esters, taurine derivatives (in particular alkyltaurides), polycondensates of ethylene oxide with phosphated tristyrylphenols and polycondensates of ethylene oxide with phosphoric esters of alcohols or phenols. The presence of at least one surfactant is often required because the active substance and/or the inert vehicle are not soluble in water and the carrier agent for the application is water.

Furthermore, particularly useful adjuvants which enhance application are natural or synthetic phospholipids from the series of the cephalins and lecithins, for example phosphatidylethanolamine, phosphatidylserine, phosphatidylglycerine or lysolecithin.

The agrochemical compositions generally contain: 0.1 to 99%, in particular 10 to 75%, more particularly 20 to 60% of the active substances (A), (B1), (B2) and (B3); the balance of the formulation comprising a solid and/or liquid carrier (such as water, for example) along with optional surfactant(s) and other optional inert ingredients known in the art such as, e.g., protective colloids, adhesives, thickeners, thixotropic agents, penetrating agents, preservatives, stabilizers, antifoaming agents, antifreeze agents, sequestering agents, dyes, pigments, colorings and polymers.

In one embodiment, commercial products will preferably be formulated as concentrates whereas the end user will normally use dilute formulations.

In a specific embodiment, the formulation containing the macrolides compound, especially abamectin, is an aqueous suspension and comprises, as formulation adjuvants, at least two surface active compounds, wherein (i) at least one surface active compound has a molecular weight of less than 2200, preferably less than 1700, such as in the range 400 to 1500, advantageously in the range 600 to 1200, and a Hydrophile-Lipophilic Balance (HLB) of at least 10, preferably in the range 10 to 25, such as 12 to 20, preferably 14 to 18 and (ii) at least one surface active compound is non-ionic, has a molecular weight of at least 2200, preferably at least 3000, such as in the range of 3500 to 15000, for example, 3500 to 10000, especially 4000 to 7500, advantageously 4500 to 6000, wherein 10 to 85, such as 15 to 80, preferably 17 to 50, % of the compound molecular weight contributes to the hydrophile constituent of the compound, and, independent of the hydrophile proportion, the molecular weight of the hydrophobe constituent of the compound is from 2000 to 10000, preferably 2400 to 3900, more preferably 3000 to 3800, such as 3200 to 3700; provided that the weight ratio of surface active compound to the macrolide compound is in the range 0.08 to 0.5, preferably 0.1 to 0.3, advantageously 0.15 to 0.25, and the weight ratio of (ii):(i) is at least 0.5, such as at least 1.0, preferably at least 1.5, especially in the range 2 to 5, advantageously in the range 2 to 3. Advantageously, three surface active compounds, one of (i) and two of (ii), are used in the formulation. Examples of a suitable surface active compound (i) is ionic, advantageously an anionic, surfactant; such as selected from a sulfate type (e.g., an aryl sulfate) and a phosphate type (such as an alkylphenol polyalkoxyether phosphate, a block copolymer of polyalkoxyether phosphate, polyarylphenol polyalkoxyether phosphate and an arylphenol polyalkoxyether phosphate), especially a phosphate type surfactant (such as a polyarylphenol polyalkoxyether phosphate). It is particularly desired that each (i) surface active compound is of the same type, a preferred type is a phosphate type surfactant. Specific examples of suitable anionic surfactants include: Sorprophor PS19 (Rhodia), Dowafax 30 C05 (Dow), Soprophor 4D384 (Rhodia) and Soprophor 3D33 (Rhodia). Examples of a suitable surface active compound (ii) is a polyalkylene oxide polymer, such as a block polymer. Specific examples are polyoxyethylene polyoxypropylene block polymers, and polyoxyethylene polyoxypropylene block polymer ethers and specific examples include Toximul 8320 (Stepan), Emulsogen 3510 (Clariant), Antarox PL/122 (Rhodia), Pluronic L101 (BASF), Pluronic L122 (BASF) and Pluronic PE 10500 (BASF).

In another embodiment, the formulation containing the macrolides compound, especially abamectin, is an aqueous suspension and comprises, as formulation adjuvants, at least two surface active compounds, wherein (a) at least one is an anionic phosphate type compound, and (b) at least one is a non-ionic alkoxylated alcohol or phenol. In an embodiment, the molecular weight of the (a) and (b) surface active compounds, independent of each other, is less than 2200, preferably less than 1700, such as in the range 400 to 1500, preferably in the range 600 to 1200. The (a) surface active compound preferably has a Hydrophile-Lipophilic Balance (HLB) of at least 10, preferably in the range 10 to 25, such as 12 to 20, preferably 14 to 18; and the (b) surface active compound preferably has a Hydrophile-Lipophilic Balance (HLB) of at least 5, preferably 7 to 20, such as 10 to 15. The weight ratio of surface active compounds (a) to (b) is generally in the range of 1:10 to 10:1, preferably, 5:1 to 1:1, especially 3:1 to 1:1. Examples of a phosphate type surfactant include an alkylphenol polyalkoxyether phosphate, a block copolymer of polyalkoxyether phosphate, a polyarylphenol polyalkoxyether phosphate and an arylphenol polyalkoxyether phosphate. Examples of alkoxylated alcohols include an alkoxylated alcohol (such as alkoxylated oil, alkoxlated alcohol having C5 to C18 carbon atoms in the alcohol). Examples of alkoxylated phenols include alkylphenol polyalkoxyether and (poly)arylphenol polyalkoxyether. Preferably, the (b) compound is an alkoxylated phenol. Specific examples of suitable anionic surfactants include: Soprophor 3D33 (Rhodia), Sorprophor PS19 (Rhodia) and Dowafax 30 C05 (Dow), and specific examples of non-ionic surfactants include: Synperonic NP (Uniqema), Soprophor BSU (Rhodia), Rhodasurf BC-610 (Rhodia), Toximul 8240 (Stepan) and Synperonic 91/4 (Uniqema).

The anionic surfactants may be present as acids or include alkali metals (such as lithium, sodium and potassium), alkali earth metals (such as calcium and magnesium), ammonium and various amines (such as alkylamines, cycloalkylamines and alkanolamines).

The Hydrophile-Lipophilic Balance (HLB) value is an index of the hydrophilic nature of a compound proposed by Griffin. The HLB value of a polyoxyethylene alkyl ether can be determined by, for example, the Griffin equation.

$$HLB \text{ value} = [(\text{molecular weight of the hydrophilic moiety})/(\text{molecular weight of the surface active compound})] \times 20$$

Groups, for example, sulfate and phosphate ions, can also contribute to the HLB value.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is preferably not meant to include those practices in which the pesticide is applied to the soil, rather than to the seed. For example, such treatments as the application of the pesticide in bands, "T"-bands, or in-furrow, at the same time as the seed is sowed are not preferably considered to be included in the present invention.

The formulation may be applied to the seeds using conventional coating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

The examples which follow are intended to illustrate and not limit the invention.

FORMULATION EXAMPLE (%=PER CENT BY WEIGHT)

Example 1

An abamectin formulation is prepared by mixing surfactant(s), thickening agent, polymer, suspension aid, a defoaming agent, a preservative and an antifreeze agent, with water until a homogeneous phase is achieved. Subsequently, abamectin is added and is mixed. The resulting mixture is then wet-milled through a so-called bead mill (Dyno, Drais, Premier for instance). The milling parameters are set in such a way that the average particle size of the resulting ground premix is within specifications (usually median particle size average at most 2.0 um). Finally, the buffer (if any) and a minor amount of water are added and the final product is mixed for at least 30 minutes.

| FS | % w/w |
| --- | --- |
| Example 1: Abamectin | 46.3 |
| Styrylphenol polyethoxyester phosphate | 1.5 |

-continued

| FS | % w/w |
|---|---|
| Propylene glycol | 5.0 |
| Tristyrenephenol with 16 moles EO | 1.0 |
| Silicone defoaming agent | 0.2 |
| Preservative | 0.06 |
| Linear polysaccharide | 0.2 |
| Water | (rest) |

Example 2

This formulation is suitable for mixtures of solid and liquid active ingredients such as a mixture of (B1), (B2) and (B3). The solid active ingredient(s) are mixed thoroughly with a portion of the emulsifiers and water and the mixture is ground thoroughly in a suitable mill. Another portion of the emulsifiers and water are mixed with the liquid active ingredient(s). The two mixtures are combined along with any other inert ingredients (such as pigments, thickeners, etc.) that are to be used in the formulation.

Example 2

| Example 2: FS | % w/w |
|---|---|
| active ingredients (azoxystrobin:fludioxonil:R-metalaxyl) (15:2.5:7.5) | 12.5 |
| Propylene glycol | 7.0 |
| Titanium dioxide | 10.0 |
| Styrylphenol polyethoxyester phosphate | 2.0 |
| Tristyrenephenol with 16 moles EO | 2.0 |
| Copolymer butanol PO/EO | 2.0 |
| Sodium Hydroxide (30%) | 0.3 |
| Silicone defoaming agent | 0.2 |
| Aqueous dispersion based on vinyl acetate and ethylene | 10.0 |
| Heteropolysaccharide | 0.35 |
| Preservative | 0.15 |
| Water | rest |

Example 3

Preparation of Tank Mix Seed Treatment Formulation

The seed treatment compositions of examples 1 and 2 are combined in a slurry with the following off-the-shelf seed treatment products: Cruiser® 5 FS (thiamethoxam) and Systhane® 40 WP (myclobutanil) in an amount sufficient to achieve an active ingredient concentration of 100 g a.i/100 Kg seed (example 1):25 g a.i/100 Kg seed (example 2):21 g a.i/100 Kg seed (myclobutanil) and 30 g a.i./100,000 seeds (thiamethoxam). The final combined composition is suitable to be applied to seed by spraying, wetting or mixing in a container having a volume of from 200 ml to 3 liters of the final combined composition per 100 kg of seed. The active ingredient is distributed uniformly on the seed surface by rotating and/or shaking the container.

No phytotoxicity is observed with cotton seeds that have been dressed with the formulation of example 3. Suitable control of disease and nematode pests are achieved.

Example 4

Biological Example

Introduction:

The assessments of the performance of disease control products as seed treatments may include: crop emergence, stand establishment and vigor ratings taken early in the season (up to 4 weeks after planting) and yields at the end of the season. "The more effective fungicide treatments can be readily identified based on the number of surviving and dead seedlings recorded at appropriate times after emergence" (Minton et al pages 252-255 in Methods of evaluating pesticides ed. K. D. Hickey, APS Press, 1986.)

The most important considerations in determining nematode population responses to control agents are collection, processing and evaluation of representative soil or root samples or both (Barker et al pages 283–296 in Methods of evaluating pesticides ed. K. D. Hickey, APS Press 1986). Barker et al. do not report that nematodes impact seedling stand establishment.

This example compares the efficacy of a three-way mixture of seed treatment fungicides: mefenoxam (CAS # 70630-17-0) applied at 3.32%, fludioxonil (CAS # 131341-86-1) applied 1.11% and azoxystrobin (CAS # 131860-33-8) applied at 6.64% in combination with abamectin (CAS # 65195-56-4 and No. 65195-55-3) used as a seed treatment to control soil borne diseases. It is reported that abamectin has no anti-bacterial or antifungal activity (Burg et al., tables 2.3 and 2.4 on pages 24–32 in Ivermectin and Abamectin ed. W. C. Campbell, Springer-Verlag, 1989).

(a) Control—(Seed Treated with Fungicide and Insecticide (No Nematicide))

A three way fungicide mixture of mefenoxam, fludioxonil and azoxystrobin in the aforementioned ratio is applied at 25 grams active ingredient per 100 kilograms seed along with the fungicide Systhane® (myclobutanil) (CAS # 88671-89-0) at 21 grams active ingredient per 100 kilograms seed.

The insecticide thiamethoxam (CAS # 153719-23-4) is also included in the slurry at 0.30 mg. per individual seed using water as the carrier. This formulation dilution is applied for one to two minutes at ambient temperature to approximately one kilogram of cottonseed in a Hege seed treater. Treated seed are air dried and then shipped and stored for approximately 2 weeks prior to planting. The thiamethoxam is known for insecticidal control.

(b) Abamectin Treated Seed

An abamectin seed treatment formulation is prepared by diluting an Abamectin 500FS seed treatment formulation containing 46.3% abamectin at a rate of 100 grams active ingredient per 100 Kg. cottonseed. To this is added the aforementioned four seed treatment fungicides and the insecticide thiamethoxam at the rates indicated, in water as a carrier. This formulation dilution was applied for one to two minutes at ambient temperature to approximately one kilogram of cottonseed in a Hege seed treater. Seed treated were allowed to air dry and shipped and stored at ambient temperature prior to planting (approximately two weeks). Abamectin is known for nematicidal control.

(c) Temik® at Plant Application

The cottonseed used in the Temik (aldicarb) (CAS # 116-06-3) plots also received the same three way mixture of seed treatment fungicides (mefenoxam+fludioxonil+azoxystrobin) at 25 grams active ingredient per 100 kilograms of seed. This seed was treated and shipped in the same manner as (a) and (b). The Temik 15 G is applied as per instructions on the commercial label at a rate of 5.6 kilograms per hectare. Temik is known for insecticidal and nematicidal control.

Therefore, each treatment has a fungicidal and insecticidal component, whereas treatments (b) and (c) also have a nematicidal component.

Trials were established at seven locations across the cotton belt using the conventional production practices. That is, seed were sown at a rate of 4 seed per foot of row in 36 inch rows using a randomized complete block trial design. The trial sites were selected with known nematode populations (Root-knot and Reniform) and fungal pathogens (*Pythium* spp, *Rhizoctonia solani*, and *Thielaviopsis bassicola*)

The following stand establishment data is collected from these trials. The variation in stand between trials is due to the recording method, per x feet of row/per plot/per acre.

TABLE 1

Stand Establishment recorded as number of living plants.

| | Cotton Plant Stand | | |
|---|---|---|---|
| Trial No. | (a) Control | (c) Temik | (b) Abamectin |
| 1. | 171 | 165 | 187 |
| 2. | 402 | 400 | 419 |
| 3. | 19 | 15 | 17 |
| 4. | 149 | 148 | 163 |
| 5. | 54600 | 50400 | 56000 |
| 6. | 39200 | 38640 | 39900 |
| 7. | 32900 | 29540 | 35000 |

The data shows that when a nematicide, such as abamectin, and a fungicide are applied as a seed treatment in the presence of nematodes and diseases, it improves the stand establishment compared to fungicide & insecticide treatment (a), and a fungicide, insecticide, and in-furrow nematicide treatment (c).

In summary, it is seen that this invention provides a new at least binary pesticidal composition for the protection of plant propagation materials. Variations may be made in proportions, procedures and materials without departing from the scope of the invention as defined by the following claims.

The invention claimed is:

1. A composition comprising as active ingredients:
   (A) a nematicidally effective amount of abamectin; and
   (B) a fungicidally effective amount of
      (B1) mefenoxam,
      (B2) fludioxonil; and
      (B3) azoxystrobin wherein the ratio of active ingredients (A):(B1):(B2):(B3) is (100–400 g):(7–10 g):(2–5 g):(15–20 g) per 100 Kg of seed.

2. A composition according to claim 1 wherein the ratio of active ingredients (A):(B1):(B2):(B3) is (100 g):(7.5 g):(2.5 g):(15 g) per 100kg of seed.

3. A composition according to claim 1 which further comprises a fungicidally effective amount of (C1) myclobutanil.

4. A composition according to claim 3 which further comprises an insecticidally effective amount of (D) an insecticide that is (D1) thiamethoxam.

5. A plant propagation material treated with a pesticidally effective amount of a pesticidal composition according to claim 1.

6. Plant propagation material according to claim 5 wherein the ratio of active ingredients (A):(B1):(B2):(B3) is (100 g): (7.5 g):(2.5 g):(15 g) per 100 kg of seed.

7. A method of protecting plant propagation material against attack by nematodes and phytopathogenic fungi which comprises treating said plant propagation material with a pesticidally effective amount of a composition according to claim 1.

8. A method according to claim 7 wherein said composition further comprises a fungicidally effective amount of (C1) myclobutanil.

9. A method according to claim 8 wherein said composition further comprises an insecticidally effective amount of (D) a neonicotinoid, that is (D1) thiamethoxam.

10. A method according to claim 7 wherein said plant propagation material is a plant seed selected from cotton, tomatoes, peppers, melons, cantaloupes, squash and cucumber.

11. A method of improving plant stand establishment of a crop of plants which comprises treating plant propagation material of the plant with a pesticidally effective amount of a composition according to claim 1.

12. A method according to claim 9 wherein said plant propagation material is a plant seed selected from cotton, tomatoes, peppers, melons, cantaloupes, squash and cucumber.

13. A method of improving plant stand establishment of a crop of plants which comprises treating plant propagation material of the plant with a pesticidally effective amount of a composition according to claim 3.

14. A method of improving plant stand establishment of a crop of plants which comprises treating plant propagation material of the plant with a pesticidally effective amount of a composition according to claim 4.

* * * * *